(12) United States Patent
Long et al.

(10) Patent No.: US 9,011,451 B2
(45) Date of Patent: Apr. 21, 2015

(54) INSTRUMENTS FOR USE IN THE IMPLANTATION OF AN ANKLE PROSTHESIS AND METHOD OF USING THE SAME

(71) Applicants: Jack F. Long, Warsaw, IN (US); Jeremiah M. Lewis, Leesburg, IN (US); Jonathan C. Lee, Mishawaka, IN (US); Chad S. McAlexander, Fort Wayne, IN (US); Michael J. Brow, Knoxville, TN (US); Conrad L. Klotz, Nappanee, IN (US)

(72) Inventors: Jack F. Long, Warsaw, IN (US); Jeremiah M. Lewis, Leesburg, IN (US); Jonathan C. Lee, Mishawaka, IN (US); Chad S. McAlexander, Fort Wayne, IN (US); Michael J. Brow, Knoxville, TN (US); Conrad L. Klotz, Nappanee, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 225 days.

(21) Appl. No.: 13/796,575

(22) Filed: Mar. 12, 2013

(65) Prior Publication Data
US 2014/0276853 A1    Sep. 18, 2014

(51) Int. Cl.
| | |
|---|---|
| *A61F 5/00* | (2006.01) |
| *A61B 17/16* | (2006.01) |
| *A61F 2/42* | (2006.01) |
| *A61B 17/17* | (2006.01) |
| *A61F 2/46* | (2006.01) |

(52) U.S. Cl.
CPC ............ *A61B 17/1682* (2013.01); *A61F 2/4202* (2013.01); *A61B 17/1739* (2013.01); *A61F 2/4684* (2013.01); *A61B 2017/1775* (2013.01); *A61F 2002/4622* (2013.01); *A61F 2002/4623* (2013.01)

(58) Field of Classification Search
CPC .................................................. A61B 17/1682
USPC .............. 606/86 R, 102, 184, 185; 623/21.18
See application file for complete search history.

(56) References Cited

U.S. PATENT DOCUMENTS

| | | | |
|---|---|---|---|
| 5,725,532 A | 3/1998 | Shoemaker | |
| 8,114,091 B2 * | 2/2012 | Ratron et al. | 606/99 |
| 2009/0254130 A1 * | 10/2009 | Wotton, III | 606/324 |
| 2010/0057216 A1 | 3/2010 | Gannoe et al. | |
| 2010/0318088 A1 | 12/2010 | Warne et al. | |
| 2013/0144351 A1 * | 6/2013 | Johnstone | 606/86 R |

FOREIGN PATENT DOCUMENTS

| | | |
|---|---|---|
| GB | 2479899 A | 11/2011 |
| WO | 2009158522 A1 | 12/2009 |

OTHER PUBLICATIONS

European Search Report for European Application No. 14155809.8-1654, Apr. 24, 2014, 5 pages.

* cited by examiner

*Primary Examiner* — Andrew Yang
(74) *Attorney, Agent, or Firm* — Barnes & Thornburg LLP

(57) ABSTRACT

Instruments for use in implanting an orthopedic ankle prosthesis includes a center-transfer instrument and a number of bone cutting blocks. A method of using such instruments is also disclosed.

17 Claims, 16 Drawing Sheets

INSTRUMENTS FOR USE IN THE IMPLANTATION OF AN ANKLE PROSTHESIS AND METHOD OF USING THE SAME

TECHNICAL FIELD

The present disclosure relates generally to an implantable ankle prosthesis, and more particularly to instruments and methods for implanting an ankle prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of an ankle replacement procedure, a tibial component is implanted into the patient's tibia, and a talar component is implanted into a patient's talus. A polymer bearing insert is positioned between the tibial component and the talar component. The articular surface of the talar component bears against the articular surface of the bearing insert.

SUMMARY

According to one aspect, an orthopedic surgical instrument for transferring a center location of a patient's tibia to the patient's talus during a total ankle arthroplasty procedure includes a first lever and a second lever pivotally coupled to the first lever. An upper handle is secured to a proximal end of the first lever, with a lower handle being secured to a proximal end of the second lever. A tibial trial component is secured to a distal end of the first lever, and an indenting spike is secured to a distal end of the second lever.

Movement of the first handle and the second handle toward one another causes movement of the indenting spike in the inferior direction.

The tibial trial component may include a platform having a superior surface and an inferior surface, and a stem secured to, and extending superiorly away from, the superior surface of the platform.

In an embodiment, the platform has a slot formed therein. The slot extends through the platform from the superior surface to the inferior surface thereof. The indenting spike extends through the slot of the platform.

A superior end of the indenting spike may be secured to the distal end of the second lever such that the superior end of the indenting spike is positioned superiorly of the platform of the tibial trial component. An inferior end of the indenting spike has a pointed tip formed therein. The inferior end of the indenting spike is positioned inferiorly of the platform of the tibial trial component.

In an embodiment, the stem of the tibial trial component has an elongated groove formed therein. The elongated groove extends in the superior/inferior direction. The indenting spike is positioned in the elongated groove so as to move within the elongated groove in the superior/inferior direction.

An alignment guide may be secured to the first lever and is configured to receive a guide pin.

According to another aspect, a method of performing a total ankle arthroplasty procedure on a tibia and talus of a patient includes inserting a center-transfer instrument such that a tibial trial component of the center-transfer instrument is received into a surgically-prepared cavity in the distal end of tibia of the patient. A first handle and a second handle of the center-transfer handle are then moved relative one another so as to urge an indenting spike of the center-transfer handle into a surgically-prepared superior surface of the talus of the patient so as to form an indentation therein.

The first handle and the second handle of the center-transfer handle may be moved toward one another to form the indentation in the surgically-prepared superior surface of the talus of the patient.

The tibial trial component may include a platform having a superior surface and an inferior surface, and a stem secured to, and extending superiorly away from, the superior surface of the platform. The center-transfer instrument is inserted such that the inferior surface of the platform is positioned on the a surgically-prepared superior surface of the talus of the patient, and the stem is positioned in a surgically-prepared slot formed in the distal end of the tibia of the patient and extending in the superior/inferior direction.

A locating pin formed in a posterior cutting block may be inserted into the indention formed in the surgically-prepared superior surface of the talus of the patient and then a bone saw blade advanced along a cutting guide surface of the posterior cutting block so as to cut a surgically-prepared posterior flat in the talus of the patient.

An anterior cutting block may then be attached to the posterior cutting block. A cutting burr may then be advanced along a cutting guide surface of the anterior cutting block so as to cut a surgically-prepared anterior flat in the talus of the patient.

The anterior cutting block may be attached to the posterior cutting block without removal of the posterior cutting block from the talus of the patient.

The anterior cutting block may then be removed from the posterior cutting block so that a fin cutting block may be secured to the posterior cutting block. A cutting burr may then be advanced along a cutting guide surface of the fin cutting block so as to cut a number of fin slots in the surgically-prepared anterior flat in the talus of the patient.

The fin cutting block may be secured to the posterior cutting block without removal of the posterior cutting block from the talus of the patient.

A sulcus cutting block may then be secured to the surgically-prepared talus of the patient. The sulcus cutting block has a pair of parallel guide rails, a sled captured within the guide rails, and a burr secured to the sled, the burr being free to rotate relative to the sled. The burr is operated while the sled is moved along the captured guide rails so as to cut a sulcus into the surgically-prepared posterior flat, superior flat, and anterior flat of the talus of the patient so as to create a finished surgically-prepared talar surface.

A talar component may then be implanted into the finished surgically-prepared talar surface.

BRIEF DESCRIPTION OF THE DRAWINGS

The detailed description particularly refers to the following figures, in which.

DETAILED DESCRIPTION OF THE DRAWINGS

Figure 1:
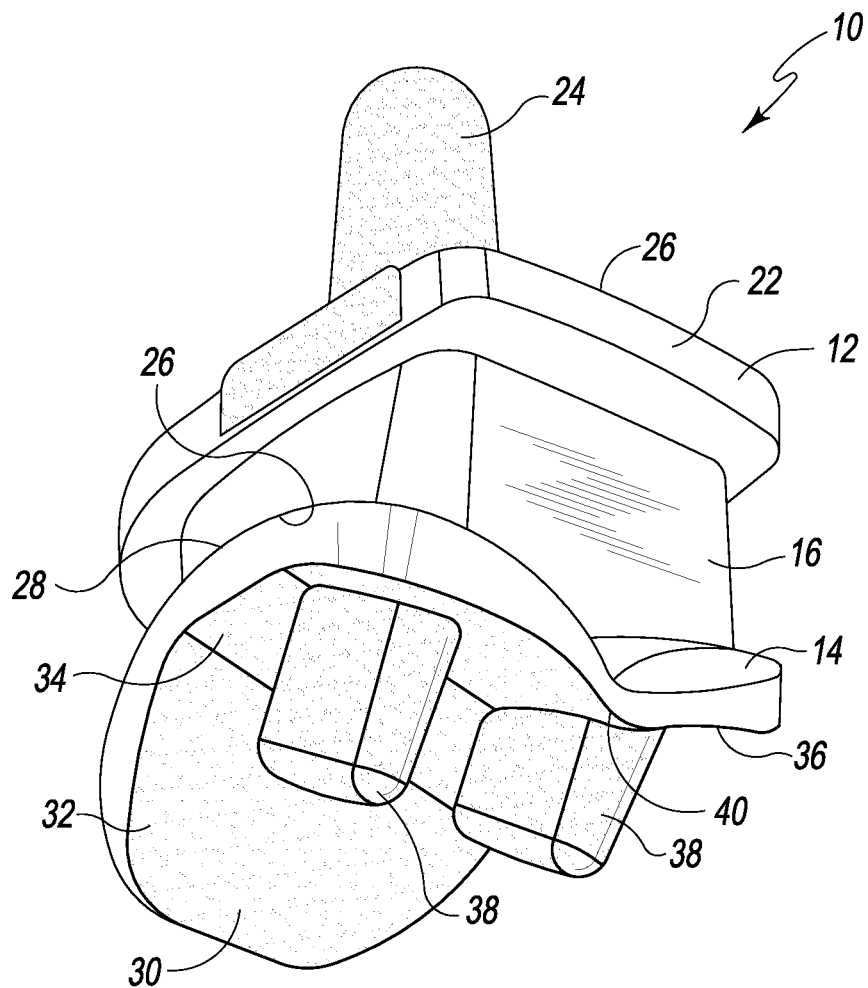
FIG. 1 is a perspective view of an orthopedic ankle prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout this disclosure in reference to both the orthopedic implants described herein and a patient's natural anatomy. Such terms have well-understood meanings in both the study of anatomy and the field of orthopedics. Use of such anatomical reference terms in the specification and claims is intended to be consistent with their well-understood meanings unless noted otherwise.

Figure 19:
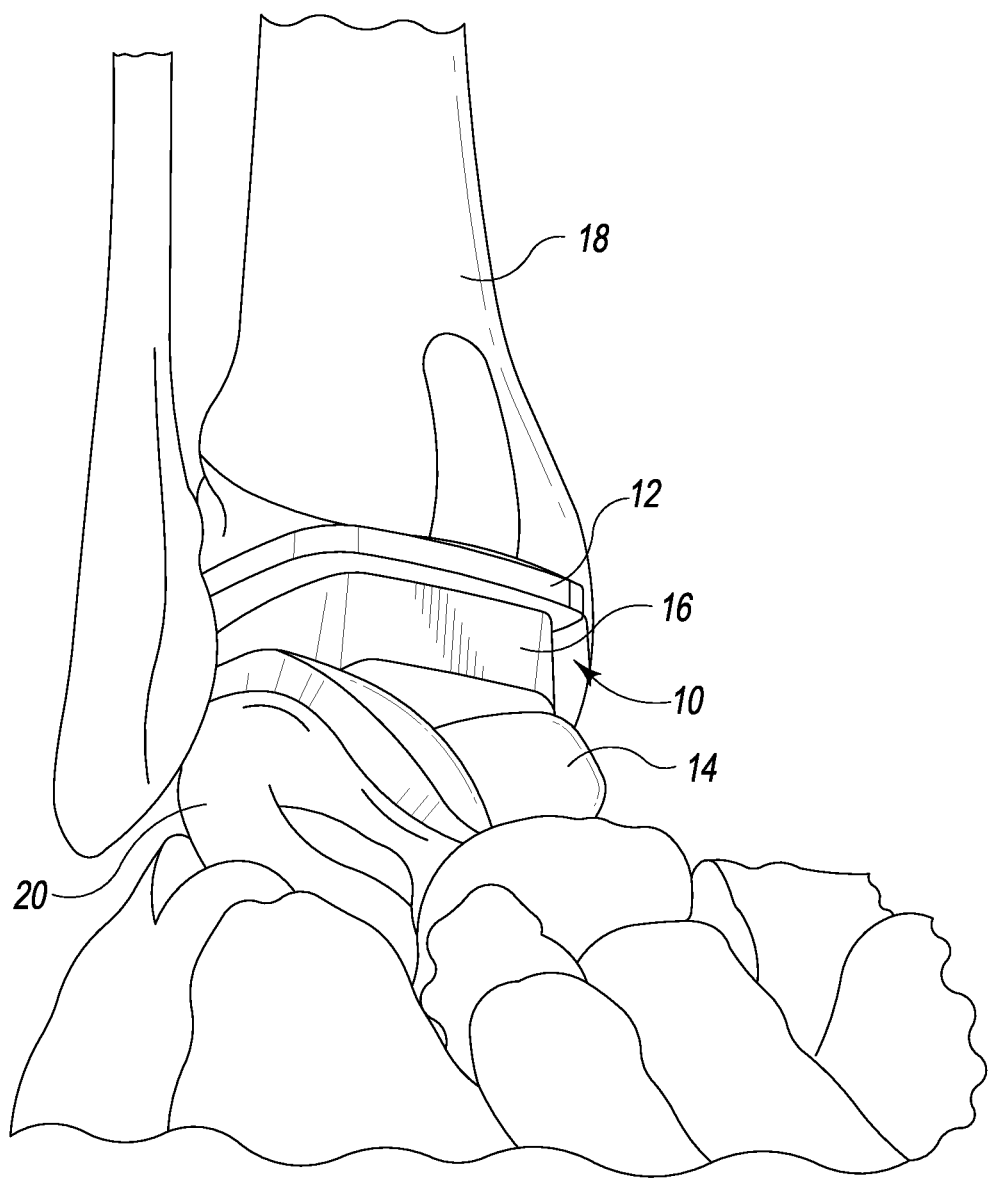

Referring now to FIG. 1, there is shown an orthopedic ankle prosthesis 10. The ankle prosthesis 10 includes a tibial component 12, a talar component 14, and a bearing insert 16. As shown in FIG. 19, the tibial component 12 is configured to be implanted into a surgically-prepared surface of the distal end of a patient's tibia 18, whereas the talar component 14 is configured to be implanted into a surgically-prepared surface of the proximal end of a patient's talus 20. In such a way, the ankle prosthesis 10 allows for flexion and extension in a manner that mimics that of a natural ankle.

The tibial component 12 includes a platform 22 having a fixation member, such as a stem 24, extending superiorly away from its superior surface 26. The stem 24 is configured to be implanted into a slot (see FIG. 19) formed in the surgically prepared distal end of a patient's tibia 18.

The bearing insert 16 is locked to the tibial component 12. In the exemplary embodiment described herein, the bearing insert 16 is snap-locked to the tibial component 16. As shown in FIG. 1, the bearing insert 16 includes a concave articular surface 26 that is configured to articulate with a convex articular surface 28 of the talar component 14. Specifically, the articular surface 26 of the bearing insert 16 is configured to emulate the configuration of the patient's natural tibial articular surfaces when the tibial component 12 is implanted into the surgically-prepared distal end of the patient's tibia 18, whereas the articular surface 28 of the talar component 14 mimics the patient's natural talar articular surfaces when the talar component 14 is implanted into the surgically-prepared proximal end of the patient's talus 20. As such, articulation between the articular surface 28 of the talar component 14 and the articular surface 26 of the bearing insert 16 mimics articulation of the patient's natural ankle.

As shown in FIG. 1, the inferior surface 30 of the talar component 14 has a geometry that includes three flat surfaces—a posterior surface 32, a superior surface 34, and an anterior surface 36. A pair of fins 38 are also formed in the inferior surface 30 of the talar component 14. The fins 38 are positioned medially and laterally of the center of the talar component 14 and extend inferiorly away from the inferior surface 30 of the talar component 14. A V-shaped ridge 40 extends along the midline of each of the flat surfaces 32, 34, 36 in the anterior/posterior direction.

The components of the ankle prosthesis 10 that engage the natural bone, such as the tibial component 12 and the talar component 14, may be constructed with a biocompatible metal, such as a cobalt chrome alloy, although other materials, such as ceramics, may also be used. The bone engaging surfaces of these components may be textured to facilitate cementing the component to the bone. Such surfaces may also be porous coated to promote bone ingrowth for permanent fixation. Moreover, the metal surfaces of the tibial component 12 that contact the bearing insert 16 may be polished.

The bearing insert 16 may be constructed with a material that allows for smooth articulation between the bearing insert 16 and the talar component 14, such as a polymeric material. One such polymeric material is polyethylene such as ultra-high molecular weight polyethylene (UHMWPE), although numerous other types of biocompatible polymers may also be used.

Referring now to FIGS. 2-12, a number of instruments for use in the surgical implantation of the ankle prosthesis are shown. The first of such instruments is a center-transfer instrument 50. As will be discussed below in more detail, the center-transfer instrument 50 is used to transfer the center location of the ankle joint, as defined by the eventual location of the tibial component 12, to the proper location on the patient's talus 20. The center-transfer instrument 50 includes a pair of levers 52, 54 pivoted together with a pivot pin 56. The proximal end of the lever 52 includes an upper handle 58, with the distal end of the lever 52 having a tibial trial component 60 formed therein or otherwise secured thereto. The proximal end of the lever 54 includes a lower handle 62, with the distal end of the lever 54 having an indenting spike 64 secured thereto.

Figure 2:
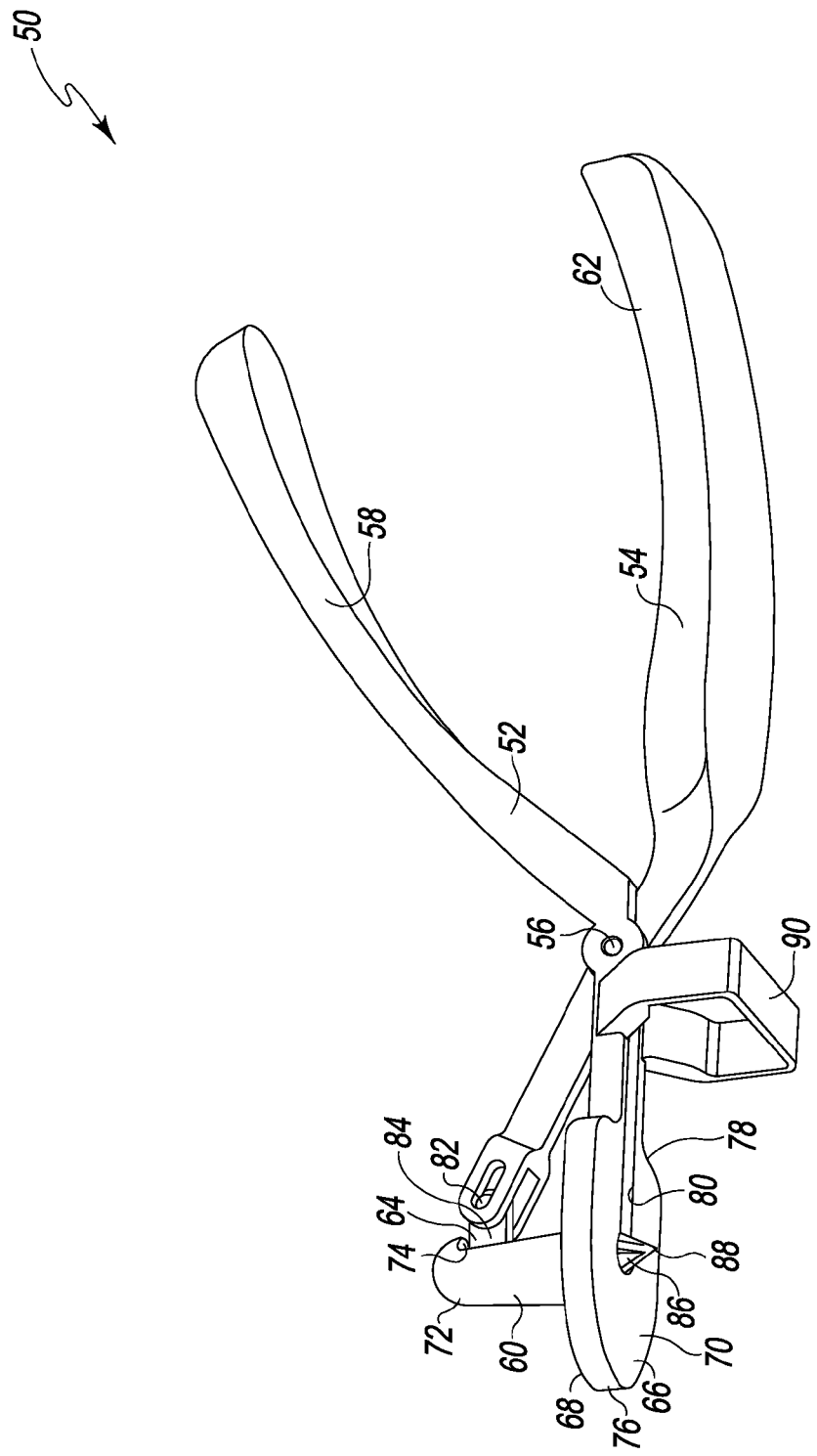
FIGS. 2 and 3 are perspective views of a center-transfer instrument.
Figure 3:
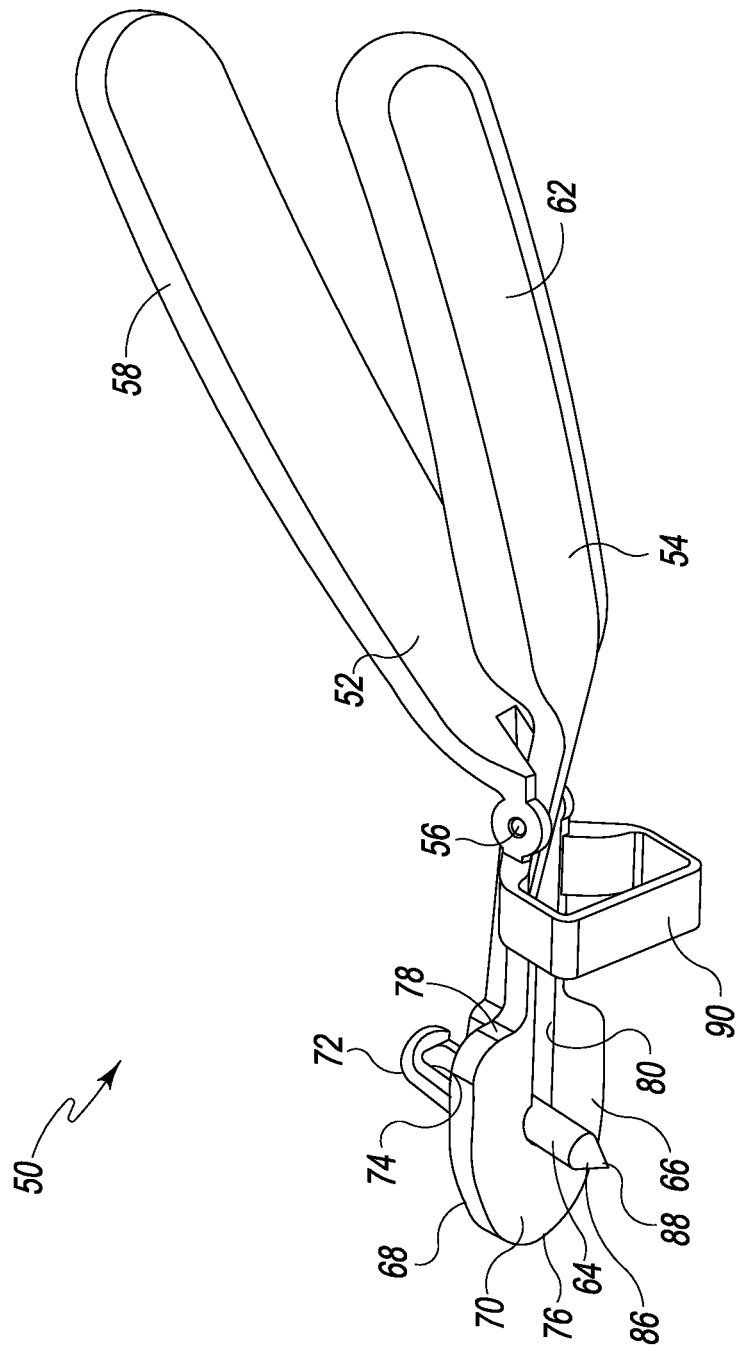

As can be seen in FIGS. 2 and 3, the tibial trial component 60 mimics the shape and geometry of the tibial component 12 and, as a result, includes a platform 66 having a superior surface 68 and an inferior surface 70. A stem 72 extends superiorly away from the platform's superior surface 68. The stem 72 has an elongated groove 74 formed in its anterior surface to receive the indenting spike 64 (as described below). The platform 66 is generally U-shaped having a rounded posterior edge 76 and a generally planar anterior edge 78. A slot 80 is formed in the platform 66. One end of the slot 80 is positioned anteriorly of the platform's anterior edge 78, with the other end of the slot 80 being formed near the middle of the platform 66. The slot 80 extends through the entire superior/inferior thickness of the platform 66—i.e., it extends from the platform's superior surface 68 to its inferior surface 70.

The lever 54 of the center-transfer instrument 50 is modular in design in that the indenting spike 64 is not integrally formed with the lower handle 62. In particular, as can be seen in FIG. 2, the indenting spike 64 is coupled to the lever 54 via a coupling pin 82. As can be seen in FIG. 3, the indenting spike 64 is captured in the elongated groove 74 formed in the stem 72 of the tibial trial component 60. As shown in FIG. 2, the superior end 84 indenting spike 64 is pin coupled to the distal end of the lever 54 such that the indenting spike 64 is maintained in a substantially vertical arrangement (i.e., it is arranged in the superior/inferior direction) as it translates superiorly and inferiorly within the elongated groove 74 formed in the stem 72.

The inferior end 86 of the indenting spike 64 defines a pointed tip 88 which, when urged into bone tissue, creates a correspondingly shaped indentation. As can be seen in FIG. 3, the indenting spike 64 extends through the slot 80 formed in the platform 66 of the tibial trial component 60. As such, when the indenting spike 64 is extended, the spike's superior end 84 is positioned superiorly of the platform's superior surface 68, with the spike's inferior end 86 (and hence its pointed tip 88) being positioned inferiorly of the platform's inferior surface 70.

When a surgeon squeezes or otherwise urges the two handles 58, 62 toward one another, the levers 52, 54 pivot about the pin 56 thereby causing the indenting spike 64 to be moved inferiorly such that its pointed tip 88 passes beyond the inferior surface 70 of the platform 66 of the tibial trial component 60. When the surgeon releases the two handles 58, 62, the levers 52, 54 are free to pivot about the pin 56 in the opposite direction so as to move the two handles 58, 62 away from one another thereby causing the indenting spike to retract (i.e., move in the opposite, superior direction).

As can be seen in FIGS. 2 and 3, an alignment guide 90 is secured to the lever 52. As will discussed below in greater detail, the alignment guide 90 is configured to receive a number of guide pins therein so as to align the center-transfer instrument 50 in a desired position.

The center-transfer instrument 50 may be constructed from a medical-grade metal such as stainless steel, cobalt chrome, or titanium, although other metals or alloys may be used.

Referring now to FIGS. 4-9, there is shown a modular cutting guide assembly 100 for use in cutting both the anterior and distal flat resections in the patient's talus 20, along with a pair of fin cuts in the talus. The cutting guide assembly 100 includes a posterior cutting block 102 for making the posterior flat resection, an anterior cutting block 104 for making the anterior flat resection, and a fin cutting block 106 for making a pair of fin cuts in the talus 20.

The posterior cutting block 102 includes an outer surface 108 and a bone-engaging surface 110 positioned opposite the outer surface 108. The outer surface 108 of the posterior cutting block 102 defines an inclined surface 112 that functions as a cutting guide surface for guiding a bone saw blade. The inclined surface 112 forms part of the block's cutting guide 114 formed near its posterior end. The cutting guide 114 is an elongated slot extending in the anterior/posterior direction. The cutting guide 114 is embodied as a captured cutting guide (i.e., it is closed on all sides so as to capture a saw blade therein). The cutting guide 114 is sized and shaped to receive the blade of a surgical saw or other cutting instrument and orient the blade to resect the posterior surface of the patient's talus.

The posterior cutting block 102 has a number of fixation holes 116 formed therein. The fixation holes 116 are sized to receive a fixation pin for pinning the posterior cutting block 102 to the patient's talus 20.

Figure 4:
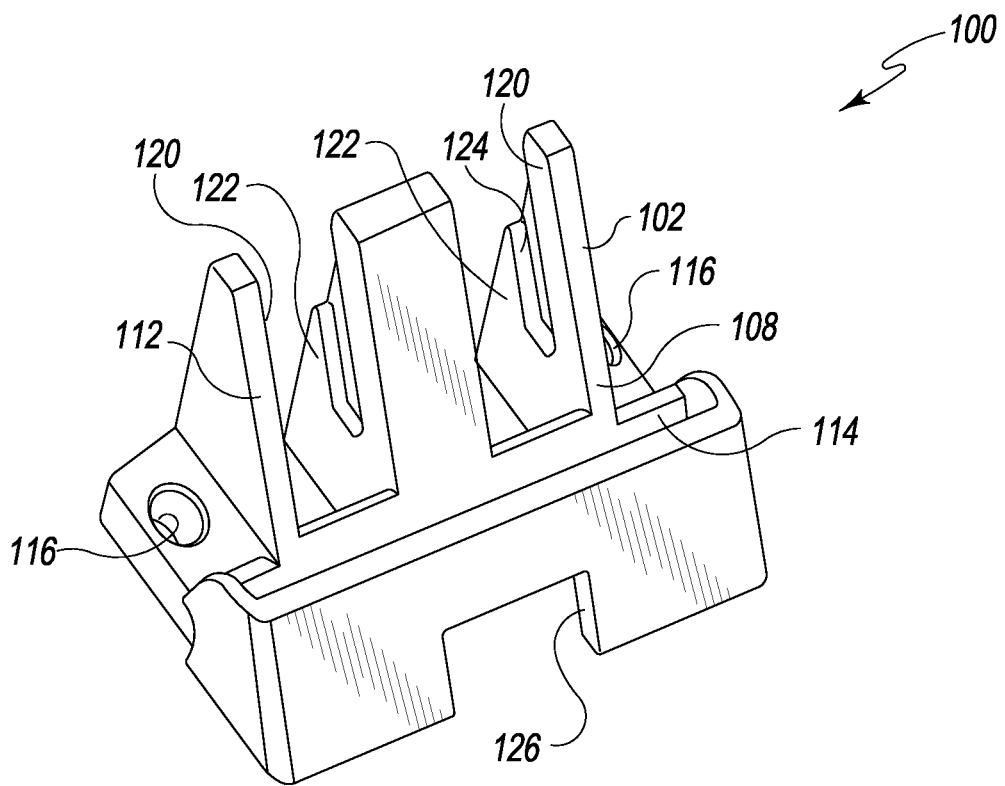
FIG. 4 is a top perspective view of a posterior cutting block.

As can be seen in FIG. 4, a locating pin 118 is secured to, and extends inferiorly away from, the bone-engaging surface 110 of the posterior cutting block 102. The locating pin 118 generally corresponds in shape and size to the pointed tip 88 of the indenting spike 64 of the center-transfer instrument 50. As will be discussed below in more detail, the locating pin 118 is inserted into the indentation formed in the bone tissue by the indenting spike 64 to position the posterior cutting block 102 in a desired location.

Figure 5:
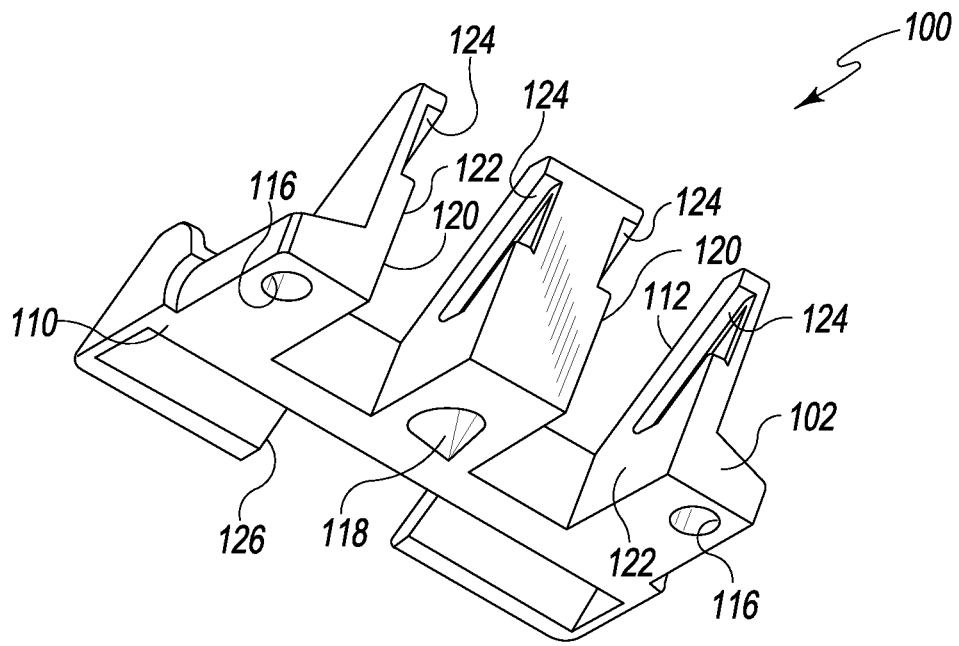
FIG. 5 is a bottom perspective view of the posterior cutting block of FIG. 4.

As can be seen in FIG. 4, the inclined guide surface 112 of the cutting block 102 is interrupted in that it has a number of docking windows 120 formed therein. As can be seen in FIG. 5, the sidewall 122 defining the docking windows 120 has a number of angled docking slots 124 formed therein. As will be discussed below, the angled docking slots 124 facilitate attachment of the anterior cutting block 104 and the fin cutting block 106 to the posterior cutting block 102.

Figure 6:
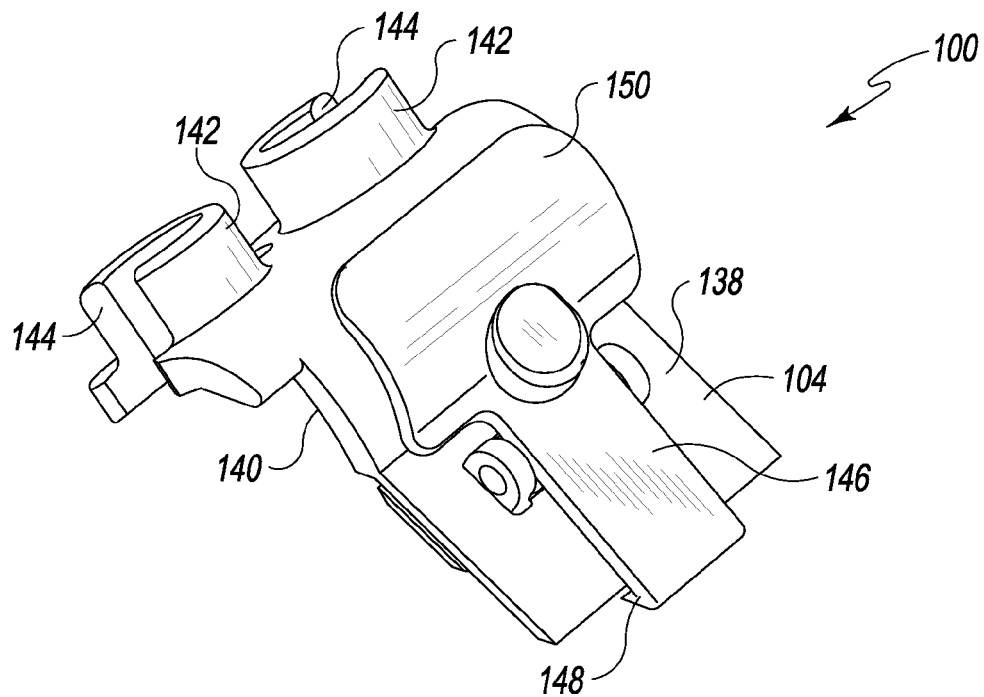
FIG. 6 is a top perspective view of an anterior cutting block.
Figure 7:
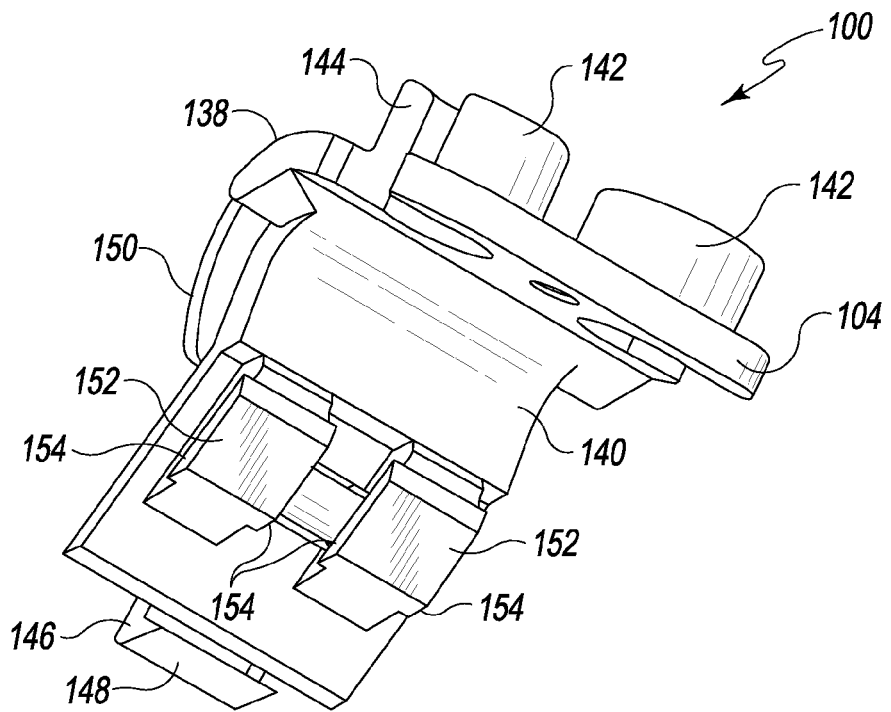
FIG. 7 is a bottom perspective view of the anterior cutting block of FIG. 6.

Referring now to FIGS. 6 and 7, there is shown the anterior cutting block 104. The anterior cutting block 104 includes an outer surface 138 and an inner surface 140 positioned opposite the outer surface 138. The anterior cutting block 104 has a pair of guide bushings 142 formed therein. The guide bushings 142 function as cutting guide surfaces for guiding a driven (i.e., power rotated) surgical burr. As can be seen in FIG. 6, one side of each of the bushings 142 has an opening 144 formed therein to permit access by the burr into the bushing 142. The bushings 142 are sized and shaped to receive the shaft (not shown) of a surgical burr and orient the burr's cutting head to resect the anterior surface of the patient's talus.

The anterior cutting block 104 has a spring-loaded clip 146 pinned to its outer surface 138. The clip 146 has a locking pawl 148 formed in its distal end and a finger grip 150 formed in its proximal end. The locking pawl 148 is spring biased downwardly in the direction toward the outer surface 138 of the anterior cutting block 104. When a surgeon pushes the grip 150, the spring bias is overcome and the pawl 148 moves upwardly away from the outer surface 138 of the anterior cutting block 104.

As can be seen in FIG. 7, a pair of mating connectors 152 having a number of alignment tabs 154 are secured to the inner surface 140 of the anterior cutting block 104. The mating connectors 152 are sized and positioned to be received into the docking windows 120 formed in the posterior cutting block 102. When doing so, the alignment tabs 154 are received into the angled docking slots 124 of the posterior cutting block 102. The spring loaded locking pawl 148 of the anterior cutting block's clip 146 engages the walls of a slot 126 formed in the posterior cutting block (see FIG. 4) to selectively lock the two blocks 102, 104 to one another.

Figure 8:
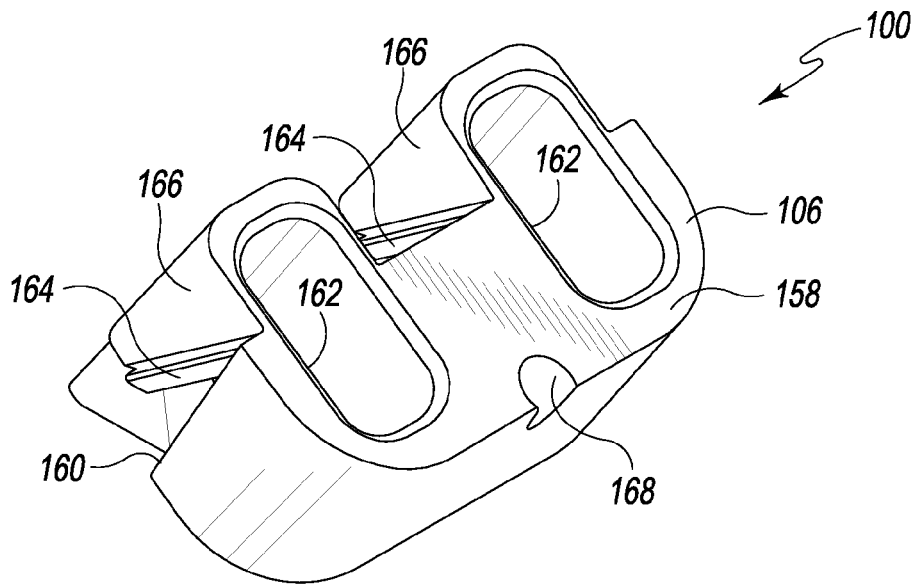
FIG. 8 is a top perspective view of a fin cutting block.
Figure 9:
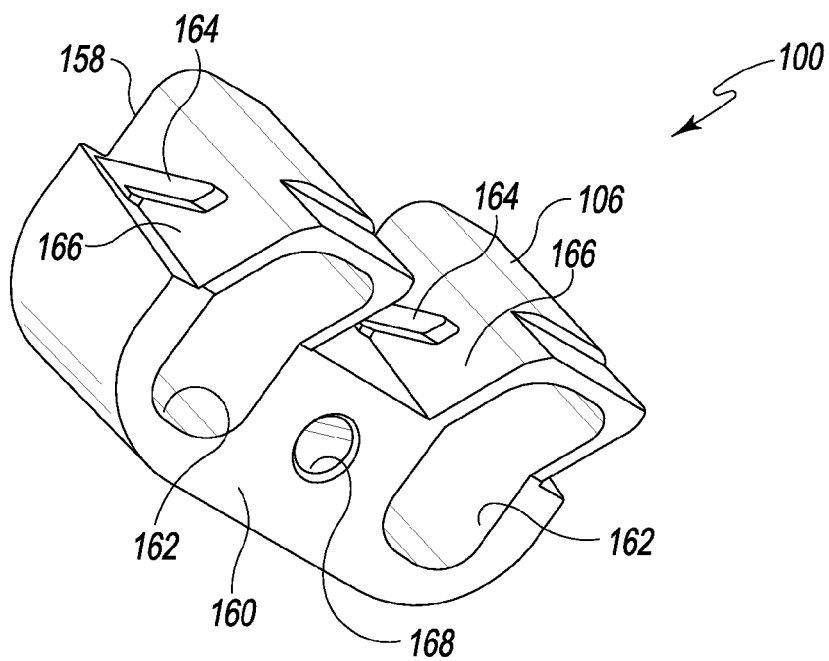
FIG. 9 is a bottom perspective view of the fin cutting block of FIG. 8.

Referring now to FIGS. 8 and 9, there is shown the fin cutting block 106. The fin cutting block 106 includes an outer surface 158 and an inner surface 160 positioned opposite the outer surface 158. The fin cutting block 106 has a pair of elongated, generally oval-shaped guide bushings 162 formed therein. The guide bushings 162 function as cutting guide surfaces for guiding a driven (i.e., power rotated) surgical burr. The bushings 162 are sized and shaped to receive the shaft (not shown) of a surgical burr and orient the burr's cutting head to form a pair of slots in the anterior surface of the patient's talus 20 to receive the pair of fins 38 formed in the inferior surface 30 of the talar component 14 (see FIG. 1).

As can be seen in FIG. 9, a number of alignment tabs 164 are formed in the sidewall 166 of the inner surface 160 that defines the lower portion of the guide bushings 162. The lower portion of the guide bushings 162 are sized and configured to be received into the docking windows 120 formed in the posterior cutting block 102. When doing so, the alignment tabs 164 are received into the angled docking slots 124 of the posterior cutting block 102. The fin cutting block 106 has a fixation hole 168 formed therein. The fixation hole 168 is sized to receive a fixation pin for pinning the fin cutting block 106 to the patient's talus 20.

Like the center-transfer instrument 50, the posterior cutting block 102, the anterior cutting block 104, and the fin cutting block 106 of the modular cutting guide assembly 100 may be constructed from a medical-grade metal such as stainless steel, cobalt chrome, or titanium, although other metals or alloys may be used.

Figure 10:
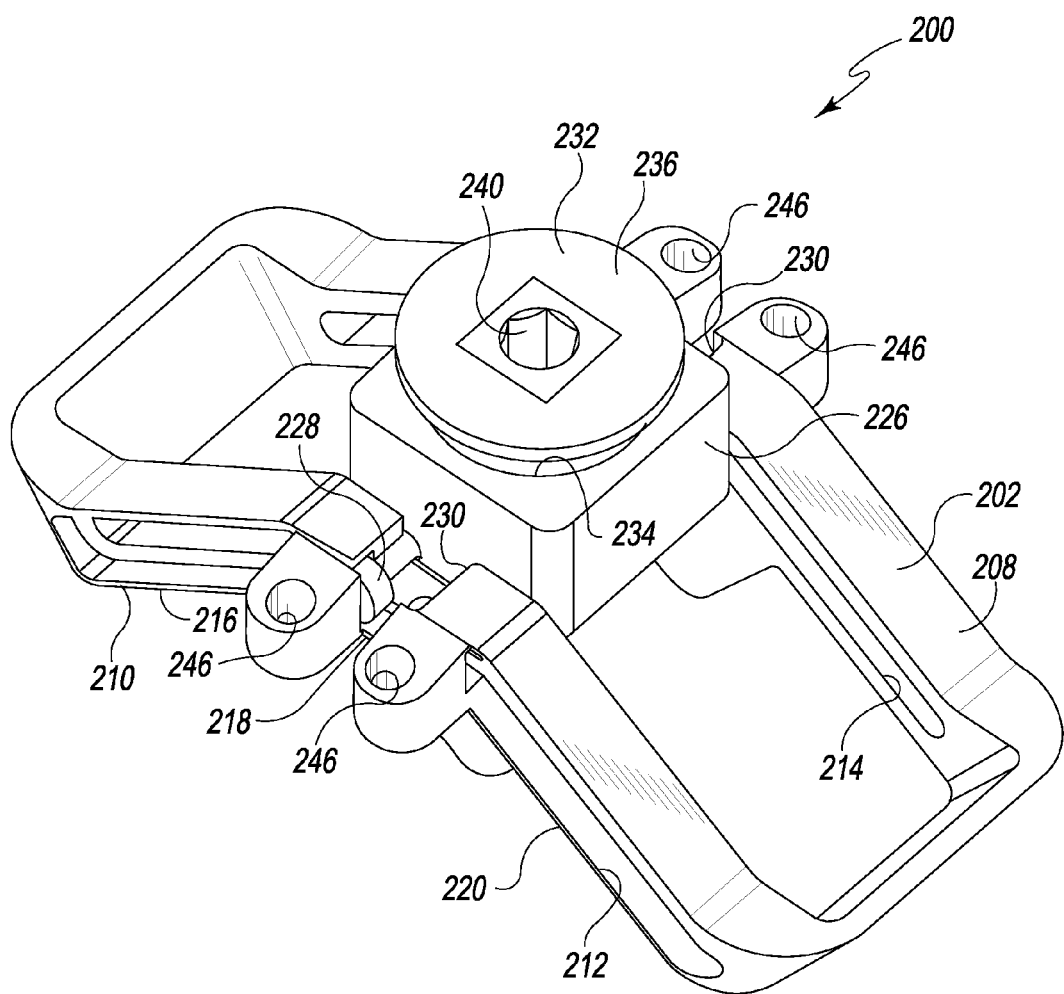
FIG. 10 is a top perspective view of a sulcus cutting block.
Figure 11:
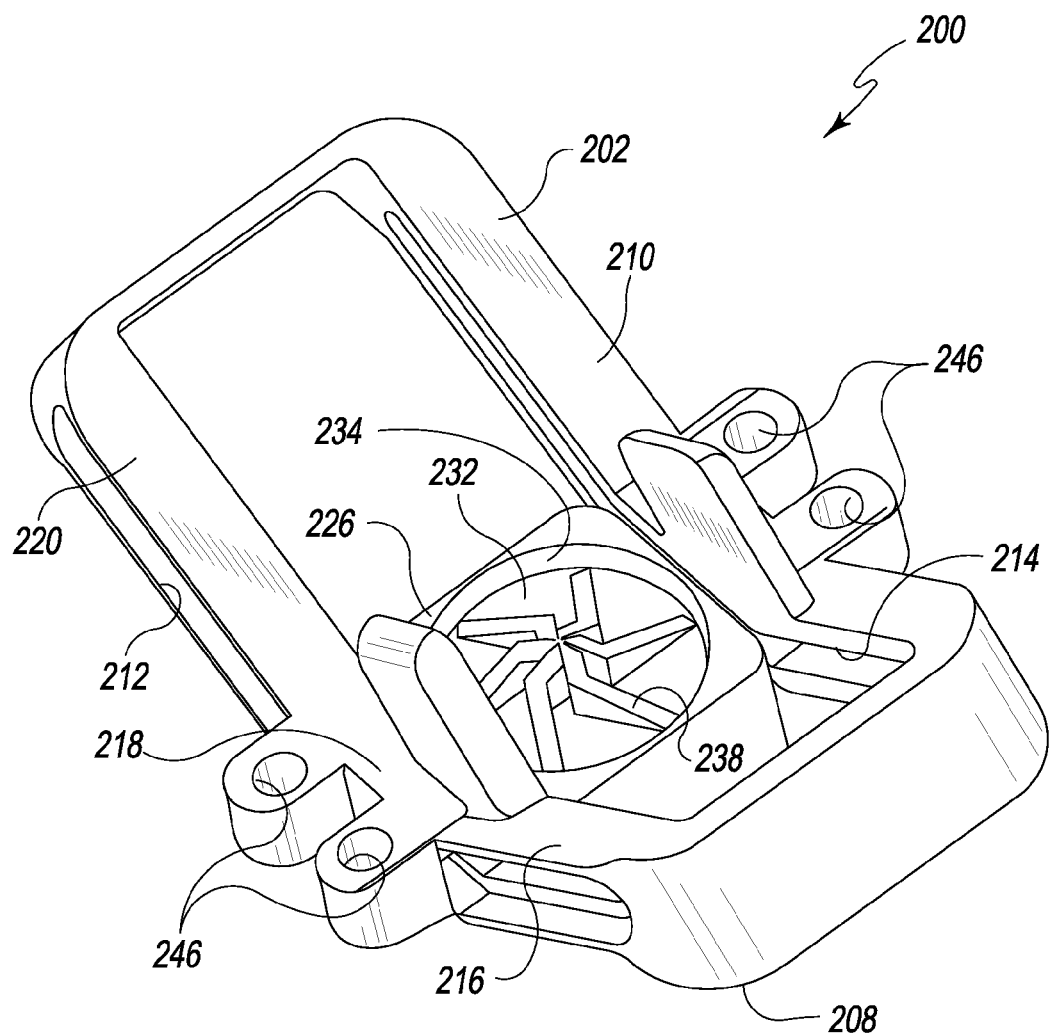
FIG. 11 is a bottom perspective view of the sulcus cutting block of FIG. 10.

Referring now to FIGS. 10 and 11, there is shown a sulcus cutting block 200 for use in cutting a sulcus in the patient's talus 20 to accommodate the V-shaped ridge 40 extending along the midline of each of the flat surfaces 32, 34, 36 of the talar component 14. The sulcus cutting block 200 includes a guide frame 202 having an outer surface 208 and a bone-engaging surface 210 positioned opposite the outer surface 208. As can be seen in FIG. 10, a pair of parallel guide rails 212, 214 are formed in the guide frame 202, with the guide rail 212 being positioned on the medial side of the block 200 and the guide rail 214 being positioned on the lateral side of the guide frame 202.

As can be seen in FIG. 11, the bone-engaging surface 210 of the guide frame 202, in essence, has three flat surfaces—a posterior surface 216, a superior surface 218, and an anterior surface 220—which correspond to the flat surfaces 32, 34, 36 of the talar component 14 and hence the corresponding flat surfaces resected into the patient's talus 20 by use of the modular cutting guide assembly 100. The guide rails 212, 214 extend in a generally parallel relationship to the flat surfaces 216, 218, 220 of the guide frame 202.

The sulcus cutting block 200 includes a sled 226 captured within the guide rails 212, 214 of the guide frame 202. The sled 226 has a pair of guide followers 228, one of which is captured in each of the guide rails 212, 214. As such, the sled 226 is free to translate back and forth along the path formed by the guide rails 212, 214. As can be seen in FIG. 10, one side of each of the guide rails 212, 214 has an opening 230 formed therein to permit the guide followers 228 and hence the sled 226 to be selectively removed from the guide rails 212, 214.

A surgical burr 232 is secured to the sled 226. The surgical burr 232 is positioned in a bore 234 formed in the sled 226 and is freely rotatable relative to the sled 226. As can be seen in FIGS. 10 and 11, a drive socket 240 of the burr 232 is positioned on the outer surface 236 of the burr 232. The output of a powered driver (not shown) may be connected to the drive socket 240 to drive (i.e., rotate) the burr 232. A cutting head 238 is formed on the opposite side of the burr 232. The cutting head 238 possesses the geometry of the desired sulcus to be cut into the patient's talus 20. As such, when the sled 226 is moved along the length of the guide rails 212, 214 while the burr 232 is being driven by a powered driver, a sulcus of a desired shape is cut into the surgically-prepared posterior, superior, and anterior surfaces of the patient's surgically-prepared talus 20 (as described below).

The guide frame 202 of the sulcus cutting block 200 has a number of fixation holes 246 formed therein. The fixation holes 246 are sized to receive a fixation pin for pinning the sulcus cutting block 200 to the patient's talus 20.

Like the other instruments described herein, the components of the sulcus cutting block 200 may be constructed from a medical-grade metal such as stainless steel, cobalt chrome, or titanium, although other metals or alloys may be used.

Figure 12:
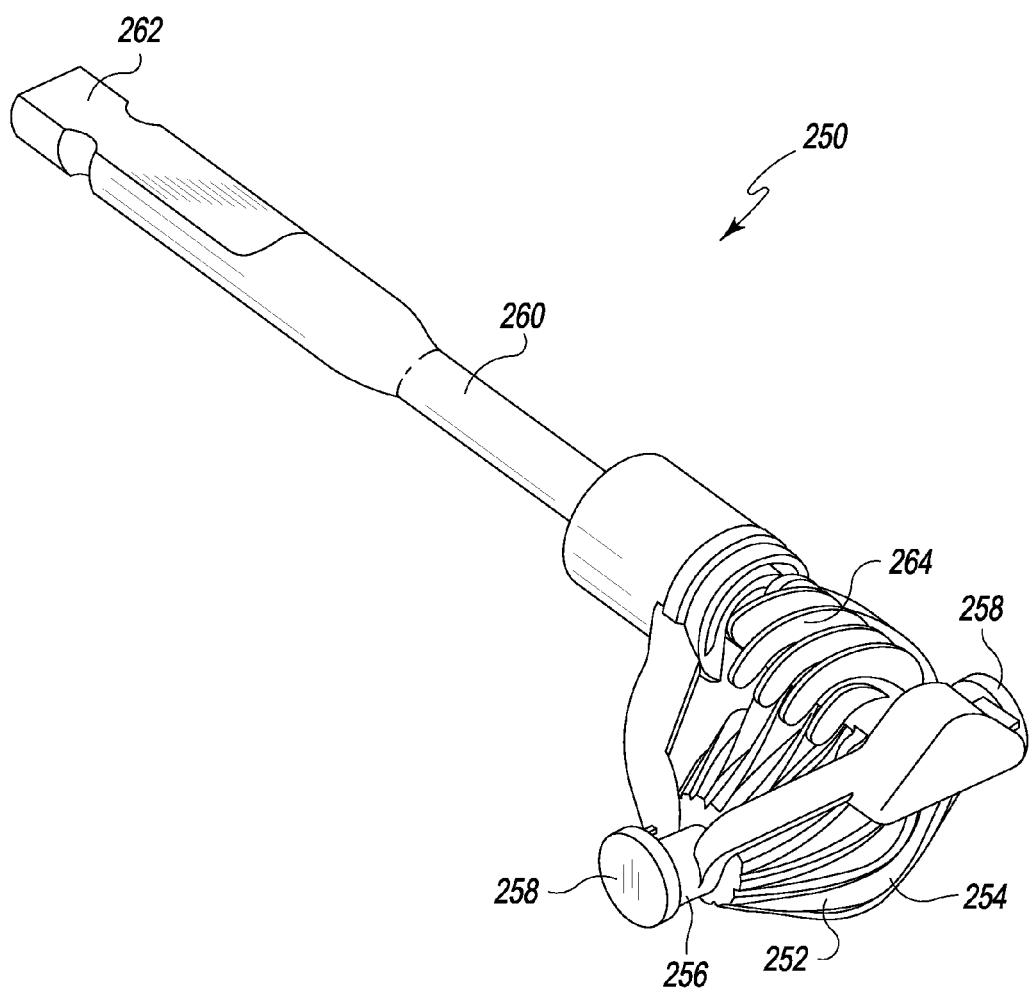
FIG. 12 is a perspective view of a cutting assembly that may alternatively be used with the guide frame of the sulcus cutting block of FIGS. 10 and 11.

Referring now to FIG. 12, there is shown another embodiment of a cutting assembly 250 for use with the guide frame 202 of the sulcus cutting block 200. The cutting assembly 250 may be used in lieu of the sled 226 and burr 232 described above in regard to FIGS. 10 and 11. The cutting assembly 250 includes a burr 252 having a cutting head 254 that possesses the geometry of the desired sulcus to be cut into the patient's talus 20. The burr 252 is supported on, and rotates freely relative to, a frame 256. The axis of rotation of the burr 252 is horizontally arranged. The frame 256 has a pair of guide followers 258, one of which may be captured in each of the guide rails 212, 214 of the guide frame 202. As such, the frame 256 of the cutting guide assembly 250 is free to translate back and forth along the path formed by the guide rails 212, 214 of the guide frame 202.

The cutting assembly 250 also includes an input shaft 260 having one end configured with a connector 262 for attaching the input shaft 260 to a powered driver (not shown), with the other end of the input shaft 260 having a worm gear 264. The worm gear 264 is intermeshed with the teeth of the burr's cutting head 254 such that rotation of worm gear 264 causes rotation of the cutting head 254. As such, when the frame 256 is moved along the length of the guide rails 212, 214 while the input shaft 260 (and hence the burr's cutting head 254) is being driven by a powered driver, a sulcus of a desired shape is cut into the surgically-prepared posterior, superior, and anterior surfaces of the patient's surgically-prepared talus 20 (as described below).

Like the other instruments described herein, the components of the cutting assembly 250 may be constructed from a medical-grade metal such as stainless steel, cobalt chrome, or titanium, although other metals or alloys may be used.

Figure 13:
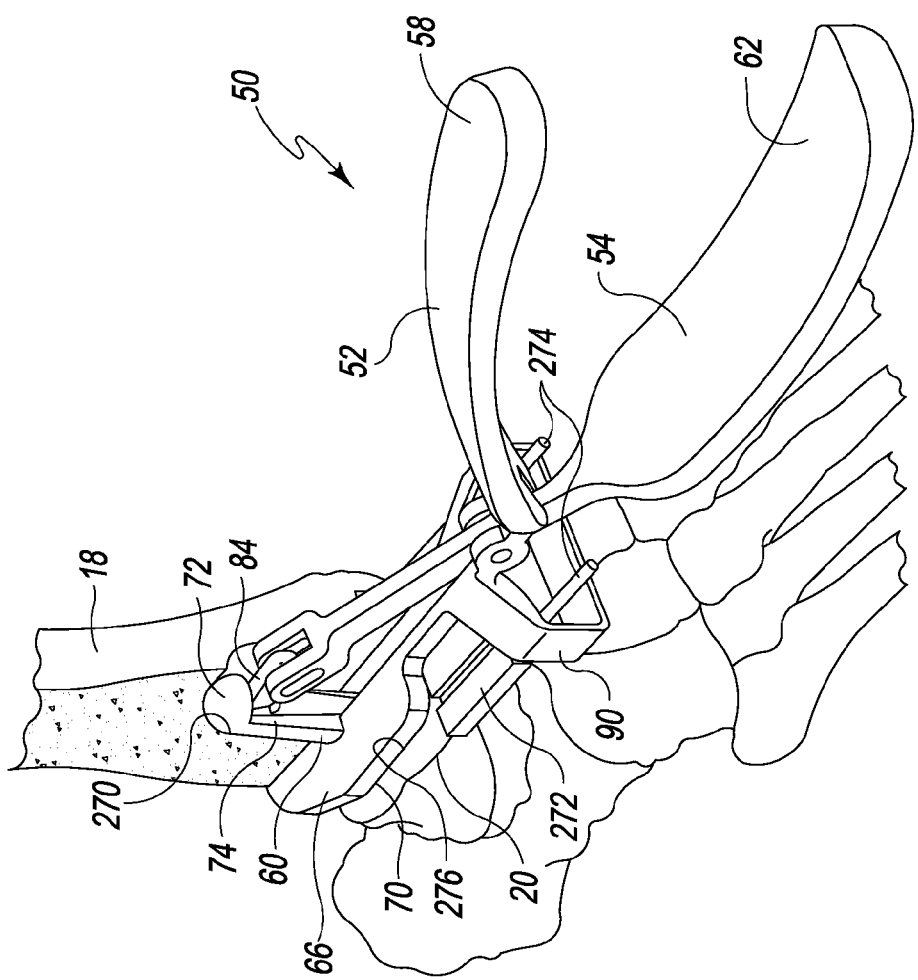
FIGS. 13-19 are perspective views of various steps of an orthopedic surgical procedure to implant the orthopedic ankle prosthesis of FIG. 1.

In operation, a surgeon may use the orthopedic instruments described herein to implant the orthopedic ankle prosthesis 10 during the performance of a total ankle arthroplasty procedure. As can be seen in FIG. 13, the center-transfer instrument 50 may be used to transfer the center location of the ankle joint, as defined by the eventual location of the tibial component 12, to the proper location on the patient's talus 20. To do so, the surgeon first inserts the tibial trial component 60 of the center-transfer instrument 50 into a surgically-prepared cavity 270 in the distal end of the patient's tibia 18 (see also FIG. 14). The surgically-prepared cavity 270 was prepared by the surgeon as part of previous steps of the overall total ankle arthroplasty procedure. As can be seen best in FIG. 14, the surgically-prepared cavity 270 is sized and shaped to receive the tibial component 12 of the orthopedic ankle prosthesis 10. As such, the tibial trial component 60 of the center-transfer instrument 10 will conform closely to the size and shape of the surgically-prepared cavity 270.

Figure 14:
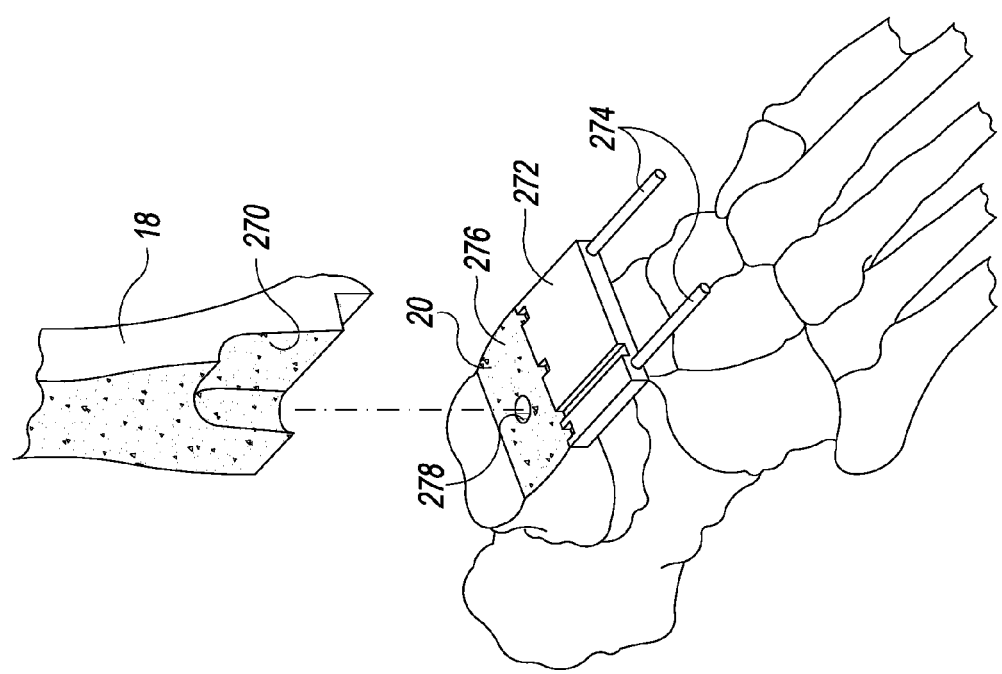

Prior to insertion of the center-transfer instrument 50, a superior cutting block 272 was pinned to the patient's talus with a pair of fixation pins 274 and thereafter used to support and guide a bone saw blade (not shown) in the resection of the superior surface of the patient's talus 20. The resultant surgically-prepared superior surface 276 is shown in FIGS. 13 and 14. The superior cutting block 272 and the fixation pins 274 are left in place on the patient's talus 20 during use of the center-transfer instrument 50. The fixation pins 274 facilitate alignment of the center-transfer instrument 50. Specifically, the instrument's alignment guide 90 receives the fixation pins 274 to align the center-transfer instrument 50 as it is being inserted into the ankle joint.

As shown in FIG. 13, the surgeon positions the patient's foot in a neutral position such that the inferior surface 70 of the platform 66 of the center-transfer instrument 50 rests on the surgically-prepared superior surface 276 of the patient's talus 20 with the remainder of the tibial trial component 60, including its stem 72, being positioned in the surgically-prepared cavity 270 in the distal end of the patient's tibia 18. With the patient's foot and the center-transfer instrument 50 so positioned, the surgeon then squeezes the two handles 58, 62 toward one another thereby causing the indenting spike 64 to be moved inferiorly and into the bone tissue of the surgically-prepared superior surface 276 of the patient's talus 20. This creates a correspondingly shaped indentation 278 in the surgically-prepared superior surface 276 of the patient's talus 20 (see FIG. 14). The location of the indentation 278 corresponds with the center of the tibial trial component 60 and hence the center of the tibial component 14 once it is subsequently implanted in the patient's tibia 18. Once the surgeon has created the indentation 278 in the surgically-prepared superior surface 276 of the patient's talus 20, the surgeon removes the center-transfer instrument 50, the superior cutting block 272, and the fixation pins 274 from the surgical site in the patient's ankle joint.

Figure 15:
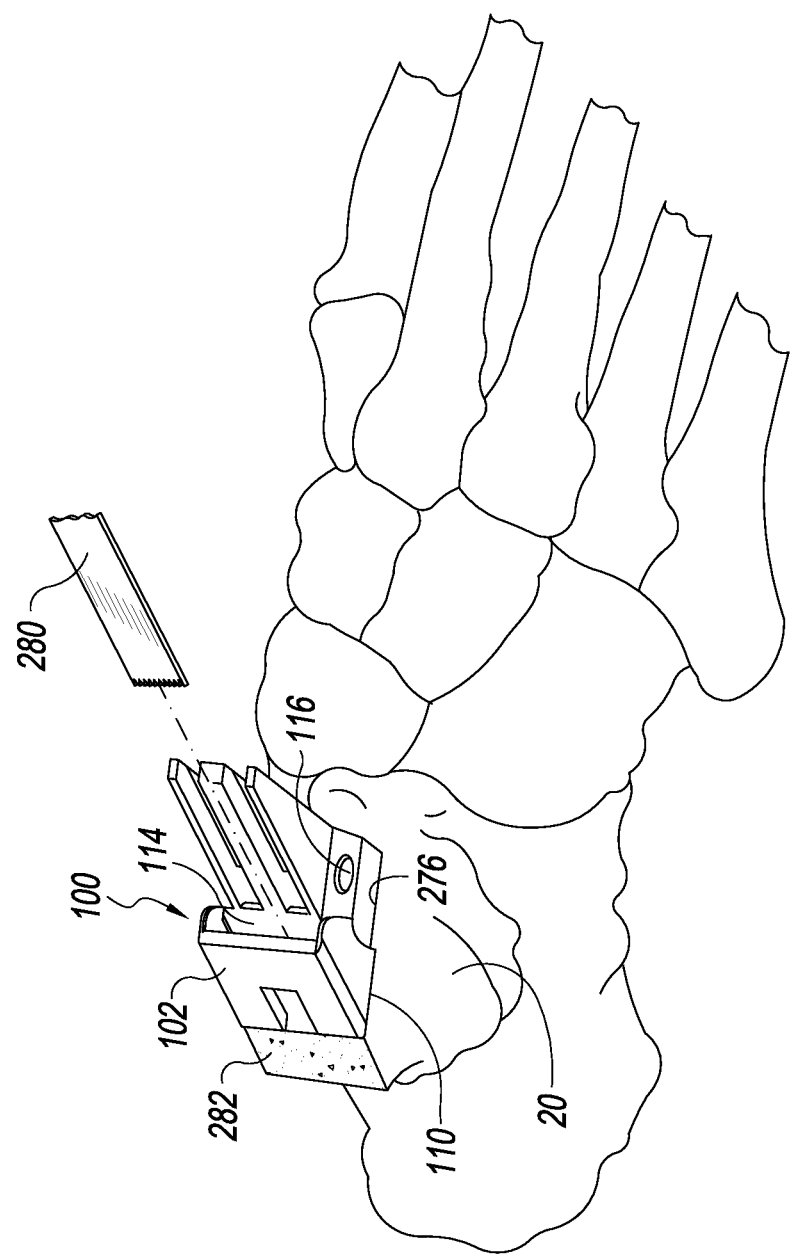

The surgeon may then utilize the modular cutting guide assembly 100 to cut the anterior and distal flat resections in the patient's talus 20, along with a pair of fin cuts in the talus 20. To do so, the surgeon first positions the posterior cutting block 102 such that the locating pin 118 formed on its bone-engaging surface 110 is positioned in the indentation 278 formed by the indenting spike 64 of the center-transfer instrument 50. The surgeon then pins the posterior cutting block 102 to the surgically-prepared superior surface 276 of the patient's talus 20 with a pair of fixation pins (not shown for clarity) inserted through the fixation holes 116. As can be seen in FIG. 15, when pinned to the talus 20 in such a manner the bone-engaging surface 110 of the posterior cutting block 102 is positioned on the surgically-prepared superior surface 276. The surgeon then advances a bone saw 280 along the cutting guide 114 of the posterior cutting block 102 to resect the posterior surface of the patient's talus 20. The resultant surgically-prepared posterior surface 282 is shown in FIG. 16.

Figure 16:
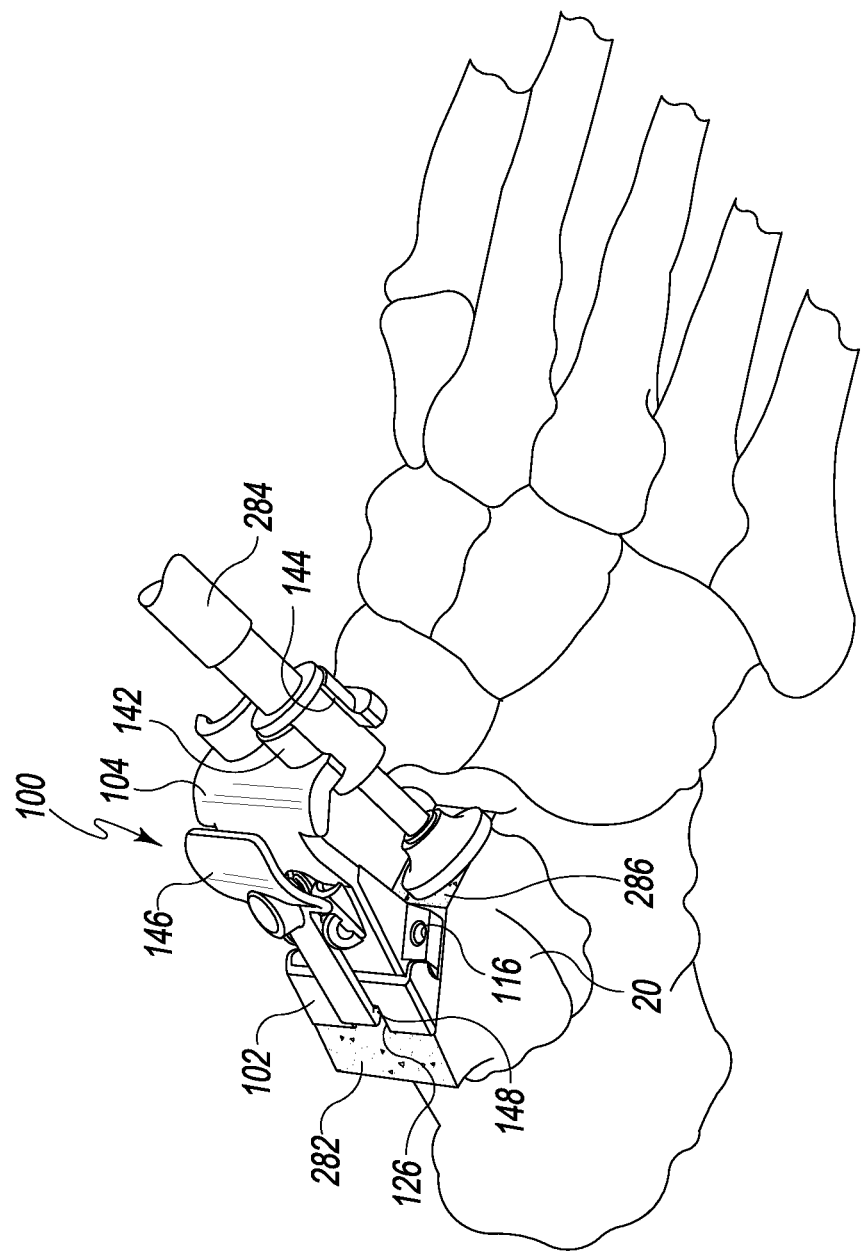

With the posterior talar resection complete, the surgeon then secures the anterior cutting block 104 to the posterior cutting block 102, as shown in FIG. 16. To do so, the surgeon inserts the mating connectors 152 of the anterior cutting block 104 (see FIG. 7) into the docking windows 120 formed in the posterior cutting block 102 (see FIGS. 4 and 5) such that the alignment tabs 154 of the anterior cutting block 104 are received into the angled docking slots 124 of the posterior cutting block 102. The spring-loaded locking pawl 148 of the anterior cutting block's clip 146 engages the walls of the slot 126 formed in the posterior cutting block 102 thereby locking the two blocks 102, 104 to one another.

Figure 17:
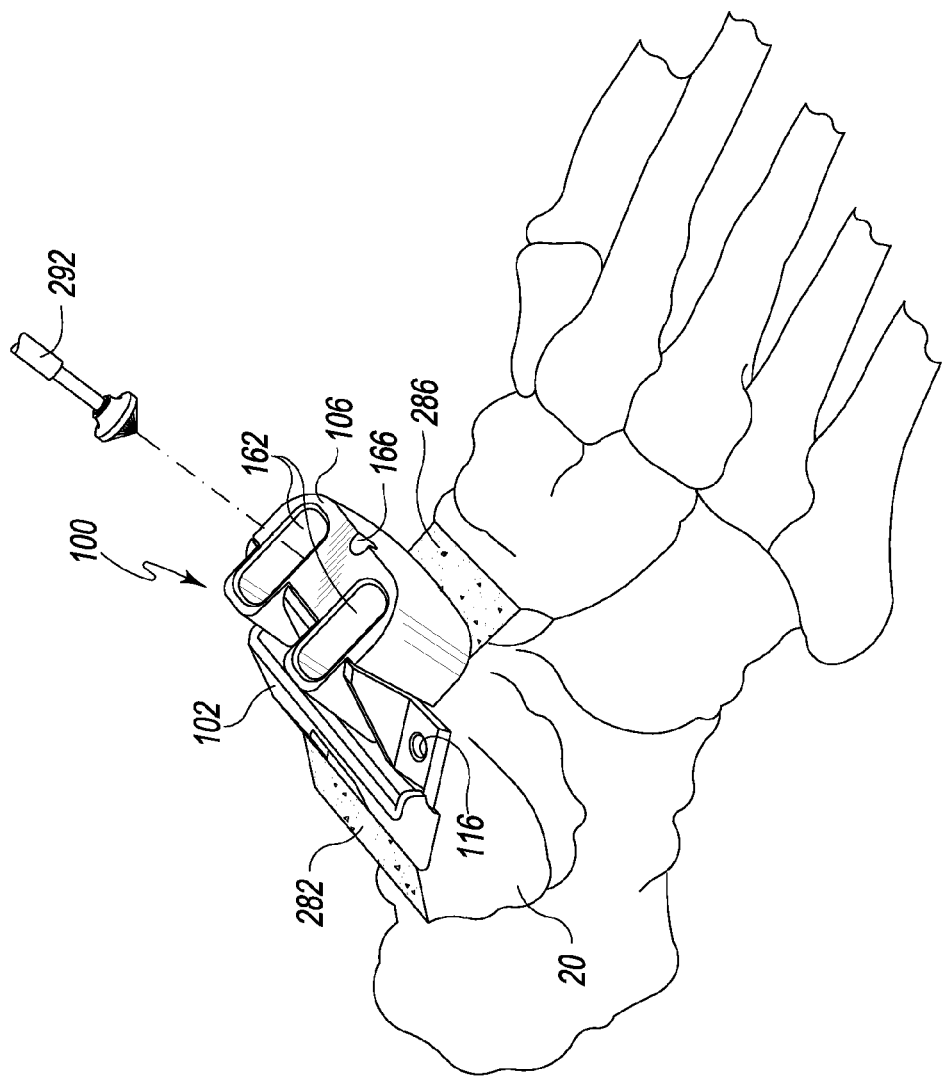

The surgeon then advances a surgical burr 284 into the opening 144 formed in one of the bushings 142 and operates the burr 284 to remove the bone tissue on the anterior surface of the patient's talus 20. The surgeon then inserts the burr 284 in the other bushing 142 and repeats the burring operation. The resultant surgically-prepared anterior surface 286 of the patient's talus 20 is shown in FIGS. 16 and 17. The surgeon then presses the grip 150 of the spring-loaded clip 146 and removes the anterior cutting block 104 from the posterior cutting block 102 while leaving the posterior cutting block 102 pinned in place.

The surgeon next secures the fin cutting block 106 to the posterior cutting block 102. To do so, the surgeon inserts the lower portion of the fin cutting block's guide bushings 162 (see FIGS. 8 and 9) into the docking windows 120 formed in the posterior cutting block 102 (see FIGS. 4 and 5) such that the alignment tabs 164 of the fin cutting block 106 are received into the angled docking slots 124 of the posterior cutting block 102. If the surgeon so desires, a fixation pin (not shown for clarity) may be inserted through the block's fixation hole 166 to pin the fin cutting block 106 to the patient's talus 20.

Figure 18:
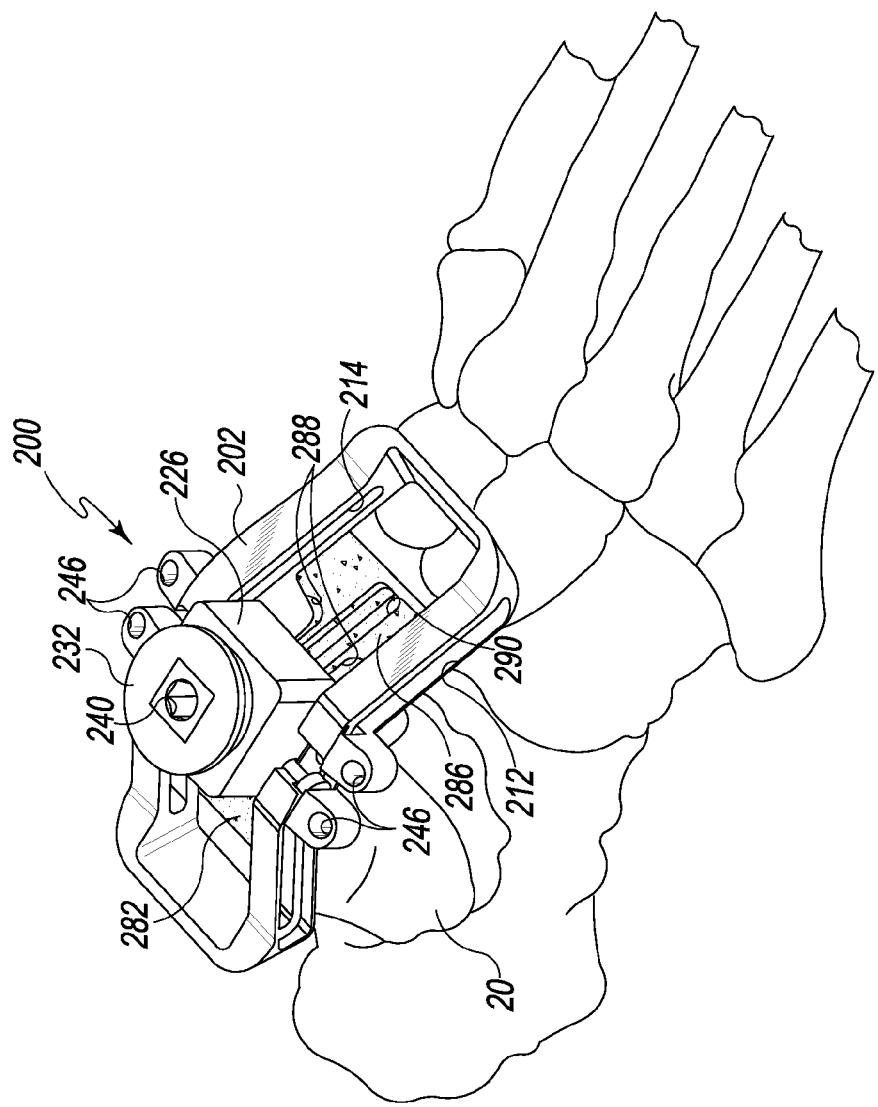

A surgical burr 292 may then be inserted into each of the bushings 162 and operated to cut a pair of slots 288 in the surgically-prepared surface of the patient's talus 20 to receive the pair of fins 38 formed in the inferior surface 30 of the talar component 14 (see FIG. 18). Once the fin slots 288 have been formed in the talus 20, the surgeon may then remove the posterior cutting block 102, the fin cutting block 106, and any remaining fixation pins.

The surgeon then secures the sulcus cutting block 200 to the talus 20 of the patient, as shown in FIG. 18. To do so, the surgeon installs the guide frame 202 of the sulcus cutting block 200 such that its bone-engaging surface 210 rests on the surgically-prepared flat surfaces 276, 282, 286 of the patient's talus 20. A number of fixation pins (not shown for clarity) are then installed through the fixation holes 246 to pin the sulcus cutting block 200 in place.

The output of a powered driver (not shown) may be connected to the burr's drive socket 240 to drive (i.e., rotate) the burr 232. With the burr's cutting head 238 being driven in such a manner, the surgeon may advance the sulcus cutting block's sled 226 along the length of the guide rails 212, 214. Doing so cuts a sulcus 290 of a desired shape into the surgically-prepared posterior surface 282, superior surface 276, and anterior surface 286 of the patient's surgically-prepared talus 20. It should be appreciated that the cutting assembly 250 of FIG. 12 may also be utilized to perform such a sulcus cut. Once the sulcus 290 has been formed in the talus 20, the surgeon may then remove the sulcus cutting block 200 and any remaining fixation pins 274 from the talus 20.

As shown in FIG. 19, with the finished surgically-prepared talar surface now formed, the surgeon may then implant the orthopedic ankle prosthesis 10 into the surgically-prepared tibia 18 and talus 20 of the patient. Thereafter, the surgeon may close the surgical wound in layers.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure as defined by the appended claims.

The invention claimed is:

1. An orthopedic surgical instrument for transferring a center location of a patient's tibia to the patient's talus during a total ankle arthroplasty procedure, comprising:
   a first lever,
   a second lever pivotally coupled to the first lever,
   an upper handle secured to a proximal end of the first lever,
   a lower handle secured to a proximal end of the second lever,
   a tibial trial component secured to a distal end of the first lever, and
   an indenting spike secured to a distal end of the second lever.

2. The orthopedic surgical instrument of claim 1, wherein movement of the first handle and the second handle toward one another causes movement of the indenting spike in the inferior direction.

3. The orthopedic surgical instrument of claim 1, wherein the tibial trial component includes:

a platform having a superior surface and an inferior surface, and a stem secured to, and extending superiorly away from, the superior surface of the platform.

4. The orthopedic surgical instrument of claim 3, wherein:

the platform has a slot formed therein, the slot extending through the platform from the superior surface to the inferior surface thereof, and the indenting spike extends through the slot of the platform.

5. The orthopedic surgical instrument of claim 4, wherein:

a superior end of the indenting spike is secured to the distal end of the second lever, the superior end of the indenting spike being positioned superiorly of the platform of the tibial trial component, and an inferior end of the indenting spike has a pointed tip formed therein, the inferior end of the indenting spike being positioned inferiorly of the platform of the tibial trial component.

6. The orthopedic surgical instrument of claim 3, wherein:

the stem of the tibial trial component has an elongated groove formed therein, the elongated groove extending in the superior/inferior direction, and the indenting spike being positioned in the elongated groove so as to move within the elongated groove in the superior/inferior direction.

7. The orthopedic surgical instrument of claim 1, further comprising an alignment guide secured to the first lever, the alignment guide being configured to receive a guide pin.

8. A method of performing a total ankle arthroplasty procedure on a tibia and talus of a patient, comprising:

inserting a center-transfer instrument such that a tibial trial component of the center-transfer instrument is received into a surgically-prepared cavity in the distal end of tibia of the patient, and moving a first handle and a second handle of the center-transfer handle relative one another so as to urge an indenting spike of the center-transfer handle into a surgically-prepared superior surface of the talus of the patient so as to form an indentation therein.

9. The method of claim 8, wherein moving the first handle and the second handle of the center-transfer handle relative one another comprises moving the first handle and the second handle of the center-transfer handle toward one another.

10. The method of claim 8, wherein:

the tibial trial component includes (i) a platform having a superior surface and an inferior surface, and (ii) a stem secured to, and extending superiorly away from, the superior surface of the platform, and inserting the center-transfer instrument comprises inserting the center-transfer instrument such that (i) the inferior surface of the platform is positioned on a surgically-prepared superior surface of the talus of the patient, and (ii) the stem is positioned in a surgically-prepared slot formed in the distal end of the tibia of the patient and extending in the superior/inferior direction.

11. The method of claim 8, further comprising:

inserting a locating pin formed in a posterior cutting block into the indention formed in the surgically-prepared superior surface of the talus of the patient, and advancing a bone saw blade along a cutting guide surface of the posterior cutting block so as to cut a surgically-prepared posterior flat in the talus of the patient.

12. The method of claim 8, further comprising:

attaching an anterior cutting block to the posterior cutting block, and advancing a cutting burr along a cutting guide surface of the anterior cutting block so as to cut a surgically-prepared anterior flat in the talus of the patient.

13. The method of claim 12, wherein attaching the anterior cutting block to the posterior cutting block comprises attaching the anterior cutting block to the posterior cutting block without removal of the posterior cutting block from the talus of the patient.

14. The method of claim 12, further comprising:

removing the anterior cutting block from the posterior cutting block, attaching a fin cutting block to the posterior cutting block, and advancing a cutting burr along a cutting guide surface of the fin cutting block so as to cut a number of fin slots in the surgically-prepared anterior flat in the talus of the patient.

15. The method of claim 14, wherein attaching the fin cutting block to the posterior cutting block comprises attaching the fin cutting block to the posterior cutting block without removal of the posterior cutting block from the talus of the patient.

16. The method of claim 14, further comprising:

attaching a sulcus cutting block to the surgically-prepared talus of the patient, the sulcus cutting block having (i) a pair of parallel guide rails, (ii) a sled captured within the guide rails, and (iii) a burr secured to the sled, the burr being free to rotate relative to the sled, and operating the burr while moving the sled along the captured guide rails so as to cut a sulcus into the surgically-prepared posterior flat, superior flat, and anterior flat of the talus of the patient so as to create finished surgically-prepared talar surface.

17. The method of claim 16, further comprising implanting a talar component into the finished surgically-prepared talar surface.

* * * * *